US012579825B2

(12) United States Patent
Fukui et al.

(10) Patent No.: US 12,579,825 B2
(45) Date of Patent: Mar. 17, 2026

(54) DRIVER STATE DETERMINATION APPARATUS, CIRCUIT AND COMPUTER PROGRAM THEREFOR

(71) Applicant: Mazda Motor Corporation, Hiroshima (JP)

(72) Inventors: Akiko Fukui, Hiroshima (JP); Yohei Iwashita, Hiroshima (JP); Koji Iwase, Hiroshima (JP); Satoru Takenaka, Hiroshima (JP); Daiki Izumoto, Hiroshima (JP)

(73) Assignee: MAZDA MOTOR CORPORATION, Hiroshima (JP)

( * ) Notice: Subject to any disclaimer, the term of this patent is extended or adjusted under 35 U.S.C. 154(b) by 513 days.

(21) Appl. No.: 18/126,496

(22) Filed: Mar. 27, 2023

(65) Prior Publication Data

US 2024/0104945 A1 Mar. 28, 2024

(30) Foreign Application Priority Data

Sep. 28, 2022 (JP) ................................. 2022-154857

(51) Int. Cl.
*G06V 20/59* (2022.01)
*A61B 5/16* (2006.01)
*A61B 5/18* (2006.01)

(52) U.S. Cl.
CPC ............ *G06V 20/597* (2022.01); *A61B 5/163* (2017.08); *A61B 5/168* (2013.01); *A61B 5/18* (2013.01)

(58) Field of Classification Search
None
See application file for complete search history.

(56) References Cited

U.S. PATENT DOCUMENTS

| | | | |
|---|---|---|---|
| 2021/0031687 A1* | 2/2021 | Kim | |
| 2022/0118985 A1* | 4/2022 | Austin | G06N 3/092 |
| 2022/0363194 A1* | 11/2022 | Windeler | H04N 7/181 |
| 2023/0192095 A1* | 6/2023 | Liu | G06V 20/597 |
| | | | 340/576 |

FOREIGN PATENT DOCUMENTS

JP 2018-198842 A 12/2018

* cited by examiner

*Primary Examiner* — Lennin R Rodriguezgonzalez
(74) *Attorney, Agent, or Firm* — XSENSUS LLP

(57) ABSTRACT

A driver state determination apparatus includes: an in-vehicle camera detecting a driver's sightline and head behavior; and a controller configured to determine the driver's state based on the driver's sightline and head behavior. When the driver is in an abnormal state based on the driver's sightline movement, the controller determines whether or not the driver's abnormal state a visual field impairment based on a change in each of a yaw angle and a pitch angle of the driver's head. When the abnormal state is the visual field impairment, the controller determines that the driver is aware of the visual field impairment when there is a direction in which the driver's sightline is not directed in the driver's field of view, and unaware of the visual field impairment when there is no direction in which the driver's sightline is not directed in the driver's field of view.

18 Claims, 4 Drawing Sheets

*FIG. 2*

DRIVER STATE DETERMINATION APPARATUS, CIRCUIT AND COMPUTER PROGRAM THEREFOR

CROSS-REFERENCE TO RELATED APPLICATION

The present application claims priority to Japanese Patent Application No. 2022-154857 filed in the Japanese Patent Office on Sep. 28, 2022, the entire contents of which being incorporated herein by reference.

TECHNICAL FIELD

Embodiments relate to a driver state determination apparatus for determining a state of a driver who drives a vehicle.

BACKGROUND ART

Conventionally, a driver state detector that detects abnormality of a driver of a vehicle has been proposed. For example, the following driver state estimation device has been proposed. The driver state estimation device determines that the driver is suspected to have the visual field defect in the case where expansion of a distribution in a direction of the driver's sightline in comparison with a normal state is detected, and a change in a steering operation from the normal state is detected (see Patent document 1).

PRIOR ART DOCUMENTS

Patent Documents

[Patent document 1] JP-A-2018-198842

SUMMARY

Problems to be Solved

As a result of research, the present inventors determined that the driver's sightline and head motion are changed according to a stage of such a disease that a visual field impairment progresses gradually like glaucoma. However, since the changes in the sightline and the head motion according to the stage of the disease are not taken into consideration in the related art as disclosed in above-described Patent document 1, it is impossible to distinguish between a stage immediately after onset of the disease and a stage at which the driver becomes aware of the disease, for example. For this reason, it may be difficult to provide appropriate driving assistance according to the driver's state.

One or more embodiments are directed to solving this and other problems and therefore has a purpose of providing a driver state determination apparatus capable of determining a type and a stage of a driver's abnormal state and providing appropriate driving assistance according to the driver's state.

Means for Solving the Problems

In order to solve the above-described problem, tone or more embodiments are directed to a driver state determination apparatus that determines a state of a driver who drives a vehicle and includes: a sightline detector that detects the driver's sightline; a head behavior detector that detects the driver's head behavior; and a controller configured to determine the driver's state based on the driver's sightline and head behavior. The controller is configured to: determine whether the driver is in an abnormal state based on movement of the driver's sightline; determine whether or not the driver's abnormal state is a visual field impairment based on a change in each of a yaw angle and a pitch angle of the driver's head when determining that the driver is in the abnormal state; determine that the driver is in a state of being aware of the visual field impairment in the case where the controller determines that the driver's abnormal state is the visual field impairment and where there is a direction in which the driver's sightline is not directed; and determine that the driver is in a state of being unaware of the visual field impairment in the case where the controller determines that the driver's abnormal state is the visual field impairment and where there is no direction in which the driver's sightline is not directed.

Accordingly, in the case where the controller determines that the driver is in the abnormal state based on the movement of the driver's sightline, the controller determines whether the driver's abnormal state is the attention dysfunction or the visual field impairment based on the change in each of the yaw angle and the pitch angle of the driver's head. Thus, a type of the abnormal state may be determined by using the head behavior that differs according to whether the driver's abnormal state is the attention dysfunction or the visual field impairment. In addition, in the case where the controller determines that the driver's abnormal state is the visual field impairment, the controller determines that the driver is in the state of being aware of the visual field impairment when there is the direction in which the driver's sightline is not directed, or determines that the driver is in the state of being unaware of the visual field impairment when there is no direction in which the driver's sightline is not directed. Thus, whether the driver is at a stage of being unaware of the visual field impairment immediately after onset of a disease, such as glaucoma, that is accompanied by the visual field impairment or the driver is at a stage of being aware of the visual field impairment after a lapse of time since the onset of the disease accompanied by the visual field impairment may be determined. In this way, the type and the stage of the driver's abnormal state can be determined. Therefore, appropriate driver assistance according to the driver's state may be provided.

The controller may be configured that, in the case where the controller determines that the driver is in the abnormal state, the controller determines that the driver's abnormal state is the visual field impairment when an amplitude of each of the yaw angle and the pitch angle of the driver's head is equal to or higher than a first threshold, or determines that the driver's abnormal state is the attention dysfunction when the amplitude of each of the yaw angle and the pitch angle of the driver's head is lower than the first threshold.

Accordingly, in the case where the driver's abnormal state is the visual field impairment and the driver tends to shake his/her head in an up-down direction and a right-left direction consciously or unconsciously in order to compensate for a visual field defect, the driver's abnormal state is the visual field impairment based on such head behavior may be determined. Thus, such a case can appropriately be distinguished from a different case, that is, a case where the driver's abnormal state is the attention dysfunction. In this way, the type of the driver's abnormal state can be determined. Therefore, appropriate driver assistance according to the driver's state may be determined.

The controller may be configured that, in the case where the controller determines that the driver is not in the abnormal state and where the controller has determined in the past that the driver's abnormal state is the visual field impairment, the controller determines that the driver is in a state where the driver has acquired compensatory action for the visual field impairment.

Accordingly, a case where the driver is in a normal state may be distinguished from the state where the driver has acquired the compensatory action for the visual field impairment. In this way, the stage of the driver's abnormal state can be determined. Therefore, appropriate driver assistance according to the driver's state may be provided.

The controller may be configured to: detect a frequency of the driver's saccade based on movement of the driver's sightline; and determine that the driver is in the abnormal state in the case where the saccade frequency is equal to or lower than a second threshold.

Accordingly, the controller determines whether the driver is in the abnormal state based on the saccade frequency. Therefore, the driver's abnormal state may be accurately determined.

The driver state determination apparatus may further include an information output device that outputs information to the driver. The controller is configured to cause the information output device to output information indicating that the driver suffers from the visual field impairment in the case where the controller determines that the driver is in the state of being unaware of the visual field impairment.

Accordingly, appropriate driver assistance may be provided to the driver who is unaware of the visual field impairment.

Advantages

According to the driver state determination apparatus according to one or more embodiments, the type and the stage of the driver's abnormal state may be determined and, thus, the appropriate driver assistance according to the driver's state may be provided.

BRIEF DESCRIPTION OF THE DRAWINGS

FIG. 2 is a block diagram of the driver state determination apparatus according to the embodiment.

DETAILED DESCRIPTION

A description will hereinafter be made on a driver state determination apparatus according to an embodiment with reference to the accompanying drawings.

[System Configuration]

Figure 1:
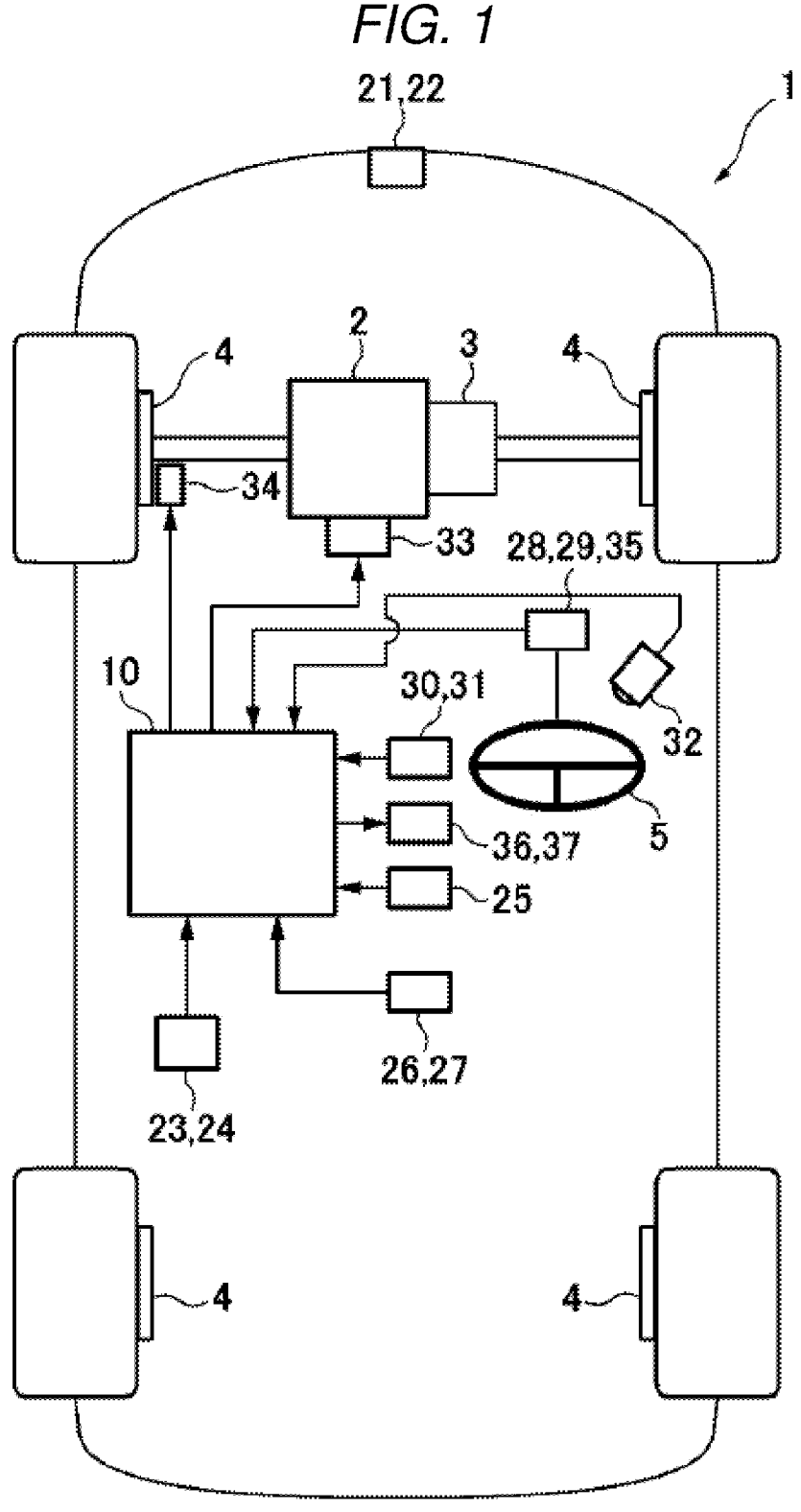
FIG. 1 is an explanatory view of a vehicle on which a driver state determination apparatus according to an embodiment is mounted.
Figure 2:
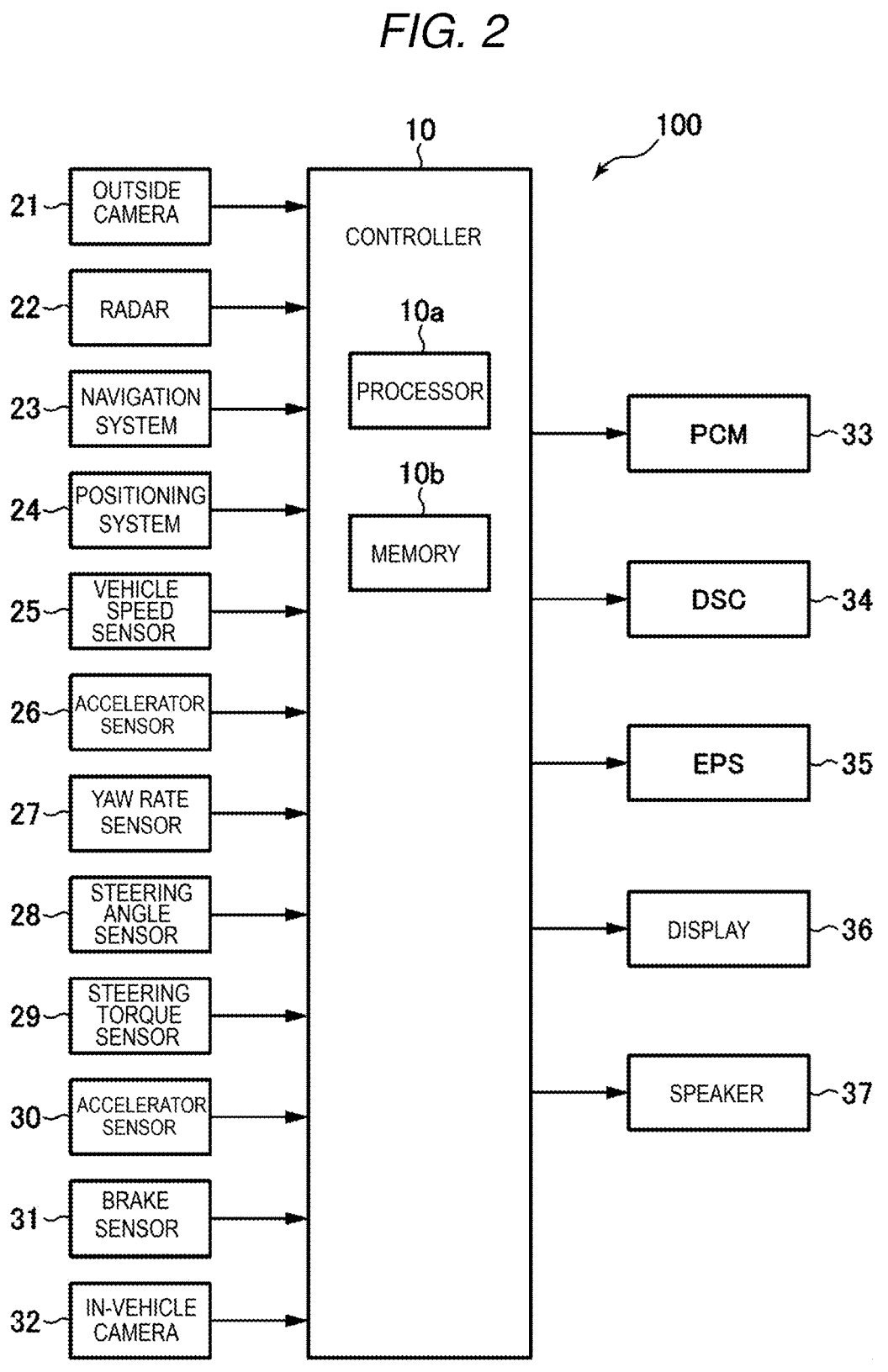

First, a description will be made on a configuration of the driver state determination apparatus according to this embodiment with reference to FIG. 1 and FIG. 2. FIG. 1 is an explanatory view of a vehicle on which the driver state determination apparatus is mounted, and FIG. 2 is a block diagram of the driver state determination apparatus.

A vehicle 1 according to this embodiment includes: drive power sources 2 such as an engine and an electric motor that output drive power; a transmission 3 that transmits the drive power output from the drive power source 2 to drive wheels; a brake 4 that applies a braking force to the vehicle 1; and a steering device 5 for steering the vehicle 1.

A driver state determination apparatus 100 is configured to determine a state of a driver of the vehicle 1 and to execute control of the vehicle 1 and driving assistance control when necessary. As illustrated in FIG. 2, the driver state determination apparatus 100 has a controller 10, plural sensors, plural control systems, and plural information output devices.

More specifically, the plural sensors include an outside camera 21 and a radar 22 for acquiring travel environment information of the vehicle 1 as well as a navigation system 23 and a positioning system 24 for detecting a position of the vehicle 1. The plural sensors also include a vehicle speed sensor 25, an acceleration sensor 26, a yaw rate sensor 27, a steering angle sensor 28, a steering torque sensor 29, an accelerator sensor 30, and a brake sensor 31 for detecting behavior of the vehicle 1 and the driver's driving operation. The plural sensors further include an in-vehicle camera 32 for detecting the driver's sightline. The plural control systems include: a powertrain control module (PCM) 33 that controls the drive power source 2 and the transmission 3; a dynamic stability control system (DSC) 34 that controls the drive power source 2 and the brake 4; and an electric power steering system (EPS) 35 that controls the steering device 5. The plural information output devices include a display 36 that outputs image information and a speaker 37 that outputs voice information.

In addition, other sensors may include a peripheral sonar that measures a distance and a position of a peripheral structure relative to the vehicle 1, a corner radar that measures approach of the peripheral structure to four corner sections of the vehicle 1, and various sensors (a heart rate sensor, an electrocardiogram sensor, a steering wheel grip force sensor, and the like) that detect the driver's state.

The controller 10 executes various arithmetic operations based on signals received from the plural sensors, transmits, to the PCM 33, the DSC 34, and the EPS 35, a control signal for appropriately actuating the drive power source 2, the transmission 3, the brake 4, and the steering device 5, and transmits, to the display 36 and the speaker 37, a control signal for outputting desired information. The controller 10 is a computer that includes one or more processors 10a (typically, a CPU), memory 10b (ROM, RAM, and the like, e.g., a non-transitory storage device) that stores various programs and data, an input/output device, and the like. As used herein 'computer' refers to circuitry that may be configured via the execution of computer readable instructions, and the circuitry may include one or more local processors 10a (e.g., CPU's), and/or one or more remote processors, such as a cloud computing resource, or any combination thereof.

The outside camera 21 captures an image, e.g., a visible image, an infrared image, or the like, around the vehicle 1 and outputs image data. The controller 10 identifies an object (a preceding vehicle, a parked vehicle, a pedestrian, a travel road, a lane marking (a lane divider, a white line, or a yellow line), a traffic signal, a traffic sign, a stop line, an intersection, an obstacle, or the like) based on the image data received from the outside camera 21.

The radar 22 measures a position and a speed of the object (particularly, the preceding vehicle, the parked vehicle, the pedestrian, a dropped object on the travel road, or the like).

For example, a millimeter-wave radar can be used as the radar 22. The radar 22 transmits a radio wave in an advancing direction of the vehicle 1, and receives a reflected wave that is generated when the object reflects the transmitted wave. Then, based on the transmitted wave and the received wave, the radar 22 measures a distance between the vehicle 1 and the object (for example, an inter-vehicular distance) and a relative speed of the object to the vehicle 1. In this embodiment, instead of the radar 22, a laser radar, an ultrasonic sensor, or the like may be used to measure the distance from and the relative speed of the object. Alternatively, the plural sensors may be used to constitute a position and speed measuring device.

The navigation system 23 stores map information therein and can provide the map information to the controller 10. Based on the map information and current vehicle position information, the controller 10 identifies a road, the intersection, the traffic signal, a building, or the like that exists around (particularly, in the advancing direction of) the vehicle 1. The map information may be stored in the controller 10. The positioning system 24 is a GPS system and/or a gyroscopic system, and detects the position of the vehicle 1 (the current vehicle position information).

The vehicle speed sensor 25 detects a speed of the vehicle 1 based on a rotational speed of a wheel or a driveshaft, for example. The acceleration sensor 26 detects acceleration of the vehicle 1. This acceleration includes acceleration in a front-rear direction of the vehicle 1 and acceleration in a lateral direction (that is, lateral acceleration) thereof. In the present specification, the acceleration includes not only a change rate of the speed in a speed increasing direction but also a change rate of the speed in a speed reducing direction (that is, deceleration).

The yaw rate sensor 27 detects a yaw rate of the vehicle 1. The steering angle sensor 28 detects a rotation angle (a steering angle) of a steering wheel of the steering device 5. The steering torque sensor 29 detects torque (steering torque) applied to a steering shaft via the steering wheel. The accelerator sensor 30 detects a depression amount of an accelerator pedal. The brake sensor 31 detects a depression amount of a brake pedal.

The in-vehicle camera 32 captures an image of the driver and outputs image data. The controller 10 detects the driver's sightline direction and behavior of the driver's head (for example, a yaw angle and a pitch angle of his/her head) based on the image data received from the in-vehicle camera 32. The in-vehicle camera 32 corresponds to an example of the "sightline detector" and the "head behavior detector" in the disclosure.

The PCM 33 controls the drive power source 2 of the vehicle 1 to adjust the drive power of the vehicle 1. For example, the PCM 33 controls an ignition plug of the engine, a fuel injection valve, a throttle valve, a variable valve mechanism, the transmission 3, an inverter that supplies electric power to the electric motor, and the like. When the vehicle 1 has to be accelerated or decelerated, the controller 10 transmits the control signal to the PCM 33 so as to adjust the drive power.

The DSC 34 controls the drive power source 2 and the brake 4 of the vehicle 1 and thereby executes deceleration control and posture control of the vehicle 1. For example, the DSC 34 controls a hydraulic pump, a valve unit, and the like of the brake 4, and controls the drive power source 2 via the PCM 33. When it is necessary to execute the deceleration control or the posture control of the vehicle 1, the controller 10 transmits the control signal to the DSC 34 so as to adjust the drive power or generate braking force.

The EPS 35 controls the steering device 5 of the vehicle 1. For example, the EPS 35 controls the electric motor, which applies the torque to the steering shaft of the steering device 5, and the like. When the advancing direction of the vehicle 1 has to be changed, the controller 10 transmits the control signal to the EPS 35 so as to change a steering direction.

The display 36 is provided in front of the driver in a cabin and displays the image information to the driver. As the display 36, for example, a liquid-crystal display or a head-up display is used. The speaker 37 is installed in the cabin and outputs various types of the voice information. Each of the display 36 and the speaker 37 corresponds to an example of the "information output device".

[Driver State Determination Processing]

Figure 3:
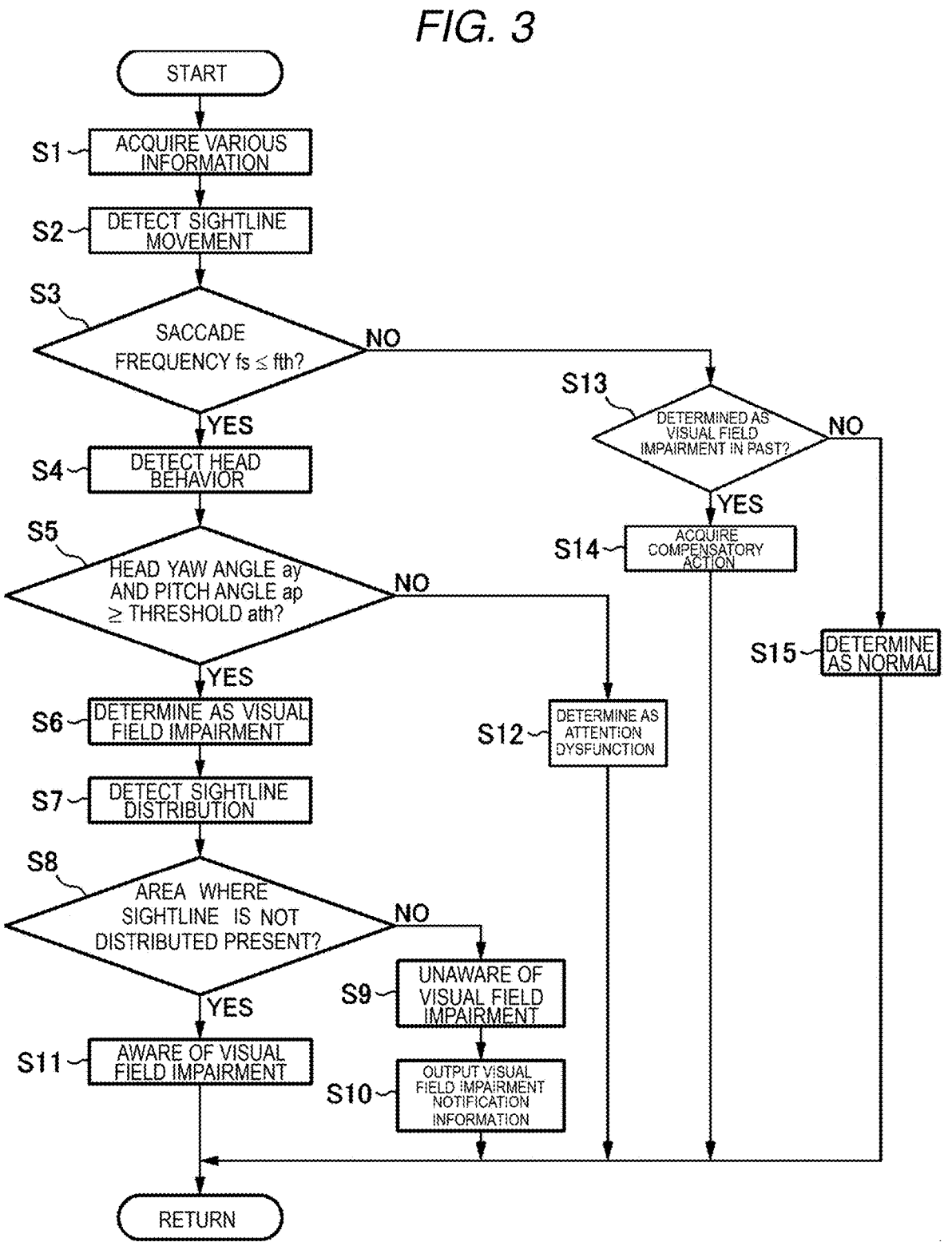
FIG. 3 is a flowchart of driver state determination processing according to the embodiment.

Next, a description will be made on a flow of driver state determination processing by the driver state determination apparatus 100 in this embodiment with reference to FIG. 3. FIG. 3 is a flowchart of driver state determination processing.

The driver state determination processing is initiated when a power supply of the vehicle 1 is turned on, and is repeatedly executed by the controller 10 in a specified cycle (for example, every 0.05 to 0.2 second).

When the driver state determination processing is initiated, first, the controller 10 acquires various types of information including the driver's sightline, i.e., where the driver is gazing, and head behavior based on the signals that are received from the sensors including the outside camera 21, the radar 22, the navigation system 23, the positioning system 24, and the in-vehicle camera 32 (step S1).

Next, the controller 10 detects movement of the driver's sightline based on the signal that is received from the in-vehicle camera 32 in step S1 (step S2). More specifically, the controller 10 detects the driver's pupils from the image (the image data) acquired by the in-vehicle camera 32, and detects the driver's sightline based on the detected pupils. Next, the controller 10 calculates a moving distance of the driver's sightline. Then, the controller 10 calculates a speed of the driver's sightline based on a temporal change in the moving distance of the driver's sightline. For example, the controller 10 calculates the speed of the driver's sightline by differentiating the moving distance of the sightline that changes over time.

Next, the controller 10 determines whether a frequency fs of the driver's saccade is equal to or lower than a threshold fth (set and stored in advance in the memory 10b, corresponding to the "second threshold" herein) based on of the driver's sightline movement detected in step S2 (step S3). More specifically, the controller 10 extracts a saccade candidate as a candidate for the saccade based on the sightline moving speed that is calculated in step S2. For example, the controller 10 extracts, as a "gaze period", a period in which a state where the sightline moving speed is lower than a predetermined speed threshold (for example, 40 deg/s) continues for a predetermined stagnation time (for example, 0.1 second). Then, the controller 10 extracts, as the "saccade candidate", the sightline movement, the moving speed of which is equal to or higher than the speed threshold (for example, 40 deg/s) and the moving distance of which is equal to or longer than a predetermined distance threshold (for example, 3 deg), from the sightline movement in a period between the two adjacent gaze periods. Furthermore, the controller 10 extracts, as the saccade, the saccade candidate, from which noise is removed by a known method. Then, in every predetermined cycle (for example, every 10 seconds), the controller 10 calculates, as the "saccade frequency fs", a value that is acquired by dividing the number of the saccades included in the cycle by a time of the cycle, and compares such a value with the threshold fth.

Figure 4:
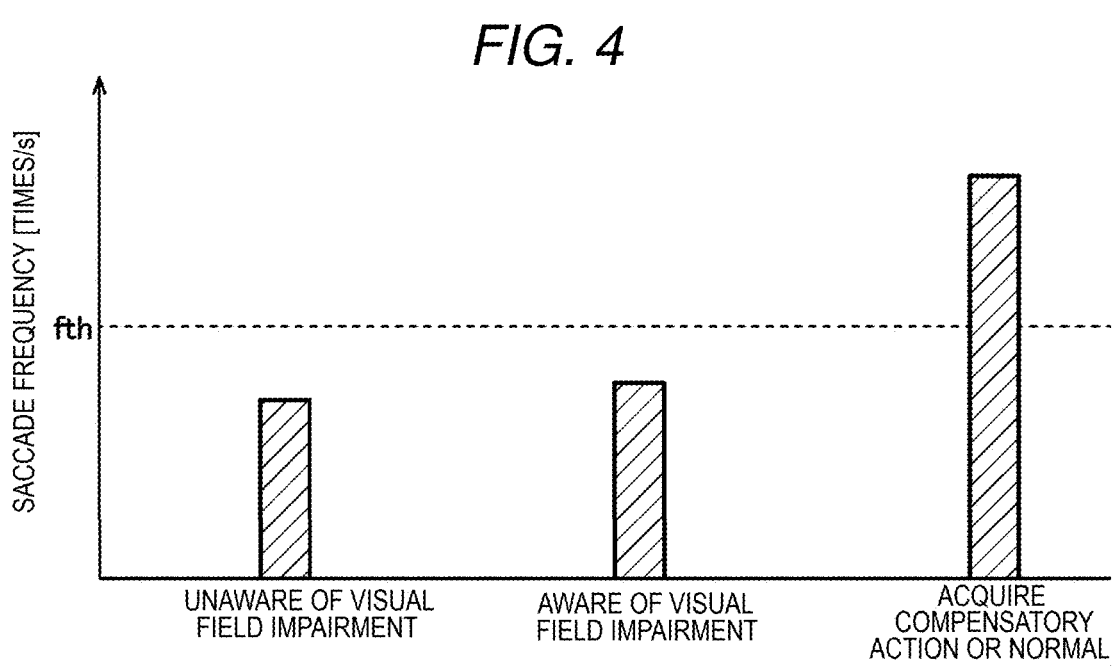
FIG. 4 is graph exemplifying a saccade frequency at each stage of a visual field impairment.

FIG. 4 is graph exemplifying the saccade frequency at each stage of a visual field impairment. As illustrated in FIG. 4, according to research by the present inventors, in the case where the driver's state is the visual field impairment, the saccade frequency is equal to or lower than the threshold fth regardless of whether the driver is aware of the visual field impairment. On the other hand, in the case where the driver's state is a normal state, or in the case where the driver has acquired action to compensate for a visual field defect through rehabilitation after suffering from the visual field impairment, the saccade frequency is higher than the threshold fth. Although not illustrated in FIG. 4, the saccade frequency is equal to or lower than the threshold fth also in the case where the driver's state is an attention dysfunction. Therefore, by determining whether the saccade frequency is equal to or lower than the threshold fth, whether the driver's state is an abnormal state (the visual field impairment or the attention dysfunction) or one of the normal state and the state where the driver has acquired the compensatory action after suffering from the visual field impairment may be determined.

Thus, as a result of the determination in step S3, if the driver's saccade frequency fs is equal to or lower than the threshold fth (step S3: YES), the controller 10 determines that the driver is in the abnormal state, and detects the driver's head behavior based on the signal that is received from the in-vehicle camera 32 in step S1 (Step S4). More specifically, from the image (the image data) that is acquired by the in-vehicle camera 32, the controller 10 recognizes the driver's head in the image and calculates a yaw angle ay and a pitch angle ap of the recognized head.

The research by the present inventors has led to such a finding that, in the case where the driver's saccade frequency fs is equal to or lower than the threshold fth such that the driver's state is the abnormal state, whether the driver's abnormal state is the attention dysfunction or the visual field impairment may further be determined based on the driver's head behavior. More specifically, in the case where the driver's abnormal state is the attention dysfunction, the driver's head behavior is not greater than that in the normal state. On the other hand, in the case where the driver's abnormal state is the visual field impairment, the driver tends to shake his/her head in an up-down direction and a right-left direction consciously or unconsciously in order to compensate for the visual field defect. As a result, the driver's head behavior is greater than that in the normal state or with the attention dysfunction. Accordingly, the driver's abnormal state may be determined to be the visual field impairment when wobbling widths of the yaw angle ay and the pitch angle ap of the driver's head are relatively large (for example, equal to or larger than specified thresholds) and that to be the attention dysfunction when the wobbling widths of the yaw angle ay and the pitch angle ap of the driver's head are relatively small (for example, smaller than the specified thresholds).

Thus, the controller 10 determines whether an amplitude of each of the yaw angle ay and the pitch angle ap of the driver's head is equal to or higher than a threshold ath (set and stored in advance in the memory 10b, corresponding to the "first threshold" herein) based on the driver's head behavior that is detected in step S4 (step S5). More specifically, in every predetermined cycle (for example, every 10 seconds), the controller 10 calculates an average value of the amplitude of the yaw angle ay and an average value of the amplitude of the pitch angle ap of the driver's head included in the cycle as the "amplitude of the yaw angle ay" and the "amplitude of the pitch angle ap", respectively, and compares each of such average values with the threshold ath.

As a result of the determination in step S5, if the amplitude of each of the yaw angle ay and the pitch angle ap of the driver's head is equal to or higher than the threshold ath (step S5: YES), the controller 10 determines that the driver's abnormal state is the visual field impairment (step S6). At this time, the controller 10 stores, in the memory 10b, information indicating that the driver's abnormal state is the visual field impairment.

Next, the controller 10 detects distribution of the driver's sightline direction based on the driver's sightline movement that is detected in step S2 (step S7). For example, the controller 10 identifies the driver's sightline direction at specified time intervals in every predetermined cycle (for example, every 10 seconds), and acquires the distribution of the sightline direction included in the cycle.

Figure 5:
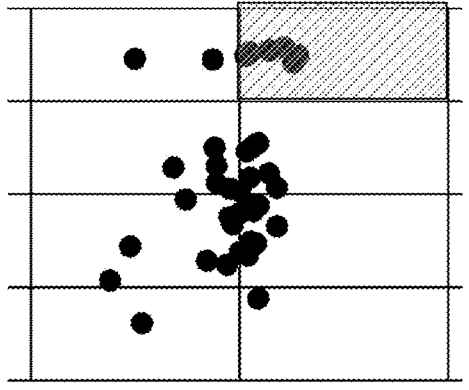
FIG. 5 is a chart exemplifying distribution of sightlines in a state of being unaware of the visual field impairment.
Figure 6:
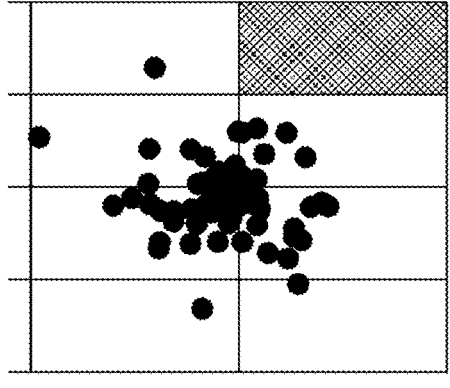
FIG. 6 is a chart exemplifying the distribution of the sightlines in a state of being aware of the visual field impairment.

FIG. 5 and FIG. 6 are views of the distribution of the sightline. FIG. 5 illustrates the distribution of the sightline in a state of being unaware of the visual field impairment, and FIG. 6 illustrates the distribution of the sightline in a state of being aware of the visual field impairment. Black circles in FIG. 5 and FIG. 6 each represent the sightline direction identified at the specified time interval in regard to the driver's visual field.

According to the research by the present inventors, in the case where the driver is not aware of the visual field impairment at a time immediately after onset of a disease such as glaucoma that is accompanied by the visual field impairment, as illustrated in FIG. 5, the distribution of the sightline in the visual field is not biased, and the direction in which the sightline is not directed does not exist yet, i.e., the driver continues to shift the sightline in an attempt to view an area having hatched lines in which the driver can no longer see. Meanwhile, in the case where time has passed since the onset of the disease accompanied by the visual field impairment, and the driver is aware of the visual field impairment, as illustrated with shading in FIG. 6, an area having cross-hatched lines where the sightline is not distributed (that is, the direction in which the sightline is not directed) exists according to a location of the visual field defect i.e., the driver no longer shifts the sightline to an area in which the driver can no longer see. Thus, by determining whether there is the area where the driver's sightline is not distributed (that is, the direction in which the sightline is not directed), whether the driver is in the state of being aware of the visual field impairment or the state of being unaware of the visual field impairment may be determined.

Thus, the controller 10 determines whether there is the area where the driver's sightline is not distributed based on the distribution of the driver's sightline direction that is detected in step S7 (step S8). As a result, as exemplified in FIG. 5, in the case where there is no area where the sightline is not distributed (that is, there is no direction in which the sightline is not directed) (step S8: NO), the controller 10 determines that the driver is in the state of being unaware of the visual field impairment (step S9). In this case, the controller 10 notifies the driver to make the driver aware of the visual field impairment, e.g., causes the display 36 and the speaker 37 to output information to notify the driver that the driver suffers from the visual field impairment (visual field impairment notification information) (step S10), and then terminates the driver state determination processing.

On the other hand, in step S8, if there is the area where the driver's sightline is not distributed (that is, there is the direction in which the sightline is not directed) (step S8: YES), the controller 10 determines that the driver is in the state of being aware of the visual field impairment (step S11). In this case, since the driver is aware of the visual field impairment, the controller 10 terminates the driver state determination processing without the output of the visual field impairment notification information.

Meanwhile, in step S5, if the amplitude of each of the yaw angle ay and the pitch angle ap of the driver's head is lower than the threshold ath (step S5: NO), the controller 10 determines that the driver's abnormal state is the attention dysfunction (step S12), and terminates the driver state determination processing. At this time, the controller 10 notifies the driver to make the driver aware of the attention dysfunction, e.g., the display 36 and the speaker 37 may output information to notify the driver that the driver suffers from the attention dysfunction.

In step S3, if the driver's saccade frequency fs is higher than the threshold fth (step S3: NO), the controller 10 determines whether the driver has been determined in the abnormal state in the past and whether such an abnormal state has been determined as the visual field impairment (step S13). For example, the controller 10 determines whether the driver's abnormal state has been determined as the visual field impairment in the past based on whether information indicating that it has been determined that the driver's abnormal state is the visual field impairment is stored in the memory 10b.

As a result, if it has been determined in the past that the driver is in the abnormal state and that the abnormal state is the visual field impairment (step S13: YES), as described with reference to FIG. 4, it is considered that, although the driver has suffered from the visual field impairment in the past, the driver has recovered to such an extent that the saccade frequency fs exceeds the threshold fth by acquiring the action to compensate for the visual field defect through the rehabilitation or the like. Thus, the controller 10 determines that the driver is in the state where the driver has acquired the compensatory action for the visual field impairment (step S14), and then terminates the driver state determination processing.

On the other hand, if it has not been determined in the past that the driver's abnormal state is the visual field impairment (step S13: NO), the controller 10 determines that the driver's state is the normal state (step S15), and terminates the driver state determination processing.

In the driver state determination processing of this embodiment, in step S3, the controller 10 determines whether the driver is in the abnormal state (the visual field impairment or the attention dysfunction) based on whether the driver's saccade frequency fs is equal to or lower than the threshold fth. However, whether the driver is in the abnormal state may be determined using another criterion. For example, in the case where an amplitude of the driver's saccade is equal to or lower than a threshold, it may be determined that the driver is in the abnormal state. Alternatively, as in the technique disclosed in JP-A-2021-077136, the amplitude and the frequency of the vehicle driver's saccade may be detected, and such an attention level may be detected that is increased as the number of caution points to be checked by the driver during the travel is increased in the external environment of the vehicle. In this way, whether the driver is in the abnormal state may be determined based on the attention level and the amplitude and the frequency of the driver's saccade.

In addition, in the driver state determination processing of this embodiment, in step S10, the controller 10 causes the display 36 and the speaker 37 to output the information to notify the driver that the driver suffers from the visual field impairment (the visual field impairment notification information). However, another type of information may be output from the display 36 and the speaker 37 according to the determination result of the driver's state, or the control signal for appropriately actuating the drive power source 2, the transmission 3, the brake 4, and the steering device 5 may be transmitted to the PCM 33, the DSC 34, and the EPS 35, so as to control the behavior of the vehicle 1.

[Operational Effects]

Next, a description will be made on operational effects of the driver state determination apparatus 100 in the above-described embodiment.

In the case where the controller 10 determines that the driver is in the abnormal state based on the movement of the driver's sightline, the controller 10 determines whether the driver's abnormal state is the attention dysfunction or the visual field impairment based on the change in each of the yaw angle ay and the pitch angle ap of the driver's head. Thus, the type of the abnormal state may be determined by using the head behavior that differs according to whether the driver's abnormal state is the attention dysfunction or the visual field impairment. In addition, in the case where the controller 10 determines that the driver's abnormal state is the visual field impairment, the controller 10 determines that the driver is in the state of being aware of the visual field impairment when there is the direction in which the sightline is not directed, or determines that the driver is in the state of being unaware of the visual field impairment when there is no direction in which the sightline is not directed. Thus, whether the driver is at the stage of being unaware of the visual field impairment immediately after the onset of the disease, such as glaucoma, that is accompanied by the visual field impairment, or the driver is at the stage of being aware of the visual field impairment after a lapse of time since the onset of the disease accompanied by the visual field impairment may be accurately determined. In this way, the type and the stage of the driver's abnormal state can be determined. Therefore, appropriate driver assistance may be provided according to the driver's state.

In the case where the controller 10 determines that the driver is in the abnormal state, the controller 10 determines that the driver's abnormal state is the visual field impairment when the amplitude of each of the yaw angle ay and the pitch angle ap of the driver's head is equal to or higher than the threshold ath, or determines that the driver's abnormal state is the attention dysfunction when such an amplitude is lower than the threshold ath. In this way, in the case where the driver's abnormal state is the visual field impairment and the driver tends to shake his/her head in the up-down direction and the right-left direction consciously or unconsciously in order to compensate for the visual field defect, the driver's abnormal state may be determined to be the visual field impairment based on such head behavior. Thus, such a case can appropriately be distinguished from a different case, that is, the case where the driver's abnormal state is the attention dysfunction. In this way, the type of the driver's abnormal state can be determined. Therefore, appropriate driver assistance may be provided according to the driver's state.

In the case where the controller 10 determines that the driver is not in the abnormal state, but the controller 10 has been determined in the past that the driver's abnormal state is the visual field impairment, the controller 10 determines that the driver has acquired the compensatory action for the visual field impairment. Thus, the case where the driver is in the normal state may be appropriately distinguished from the state where the driver has acquired the compensatory action for the visual field impairment. In this way, the stage of the driver's abnormal state can be determined. Therefore, appropriate driver assistance according to the driver's state may be provided.

In addition, since controller 10 determines whether the driver is in the abnormal state based on the saccade frequency, the driver's abnormal state maybe accurately determined.

The driver state determination apparatus 100 further includes the display 36 and the speaker 37, each of which outputs the information to the driver. When determining that the driver is in the state of being unaware of the visual field impairment, the controller 10 causes the display 36 and the speaker 37 to output the information indicating that the driver suffers from the visual field impairment. Therefore, appropriate driver assistance may be provided to the driver who is unaware of the visual field impairment.

No claim element herein is to be construed under the provisions of 35 U.S.C. 112(f) unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

The present disclosure is not limited to only the above-described embodiments, which are merely exemplary. It will be appreciated by those skilled in the art that the disclosed systems and/or methods can be embodied in other specific forms without departing from the spirit of the disclosure or essential characteristics thereof. The presently disclosed embodiments are therefore considered to be illustrative and not restrictive. The disclosure is not exhaustive and should not be interpreted as limiting the claimed invention to the specific disclosed embodiments. In view of the present disclosure, one of skill in the art will understand that modifications and variations are possible in light of the above teachings or may be acquired from practicing of the disclosure. The scope of the invention is indicated by the appended claims, rather than the foregoing description.

DESCRIPTION OF REFERENCE SIGNS AND NUMERALS

1 Vehicle
10 Controller
100 Driver state determination apparatus
21 Outside camera
22 Radar
23 Navigation system
24 Positioning system
25 Vehicle speed sensor
26 Acceleration sensor
27 Yaw rate sensor
28 Steering angle sensor
29 Steering torque sensor
30 Accelerator sensor
31 Brake sensor
32 In-vehicle camera
36 Display
37 Speaker

The invention claimed is:

1. A driver state determination apparatus for determining a state of a driver who drives a vehicle, the driver state determination apparatus comprising:

a sightline detector that detects the driver's sightline;
a head behavior detector that detects the driver's head behavior; and
a controller configured to determine the driver's state based on the driver's sightline and head behavior, wherein the controller is configured to:

determine whether the driver is in an abnormal state based on movement of the driver's sightline;

on condition that the driver is in the abnormal state, determine whether the driver's abnormal state is a visual field impairment or not based on a change in each of a yaw angle and a pitch angle of the driver's head;

on condition that the driver's abnormal state is the visual field impairment, determine that the driver is aware of the visual field impairment when there is a direction in which the driver's sightline is not directed within a visual field of the driver; and determine that the driver is unaware of the visual field impairment when there is no direction in which the driver's sightline is not directed within a visual field of the driver.

2. The driver state determination apparatus according to claim 1, wherein, on condition that the driver's abnormal state is not the visual field impairment that the controller is configured to determine that the driver's abnormal state is an attention dysfunction.

3. The driver state determination apparatus according to claim 2, wherein, on condition that the driver's abnormal state is in the abnormal state, the controller is configured to determine that the driver's abnormal state is the visual field impairment when an amplitude of each of the yaw angle and the pitch angle of the driver's head is equal to or higher than a first threshold, and determine that the driver's abnormal state is the attention dysfunction when the amplitude of each of the yaw angle and the pitch angle of the driver's head is lower than the first threshold.

4. The driver state determination apparatus according to claim 3, wherein the controller is configured to determine, in the case where the controller determines that the driver is not in the abnormal state and where the controller has determined in the past that the driver's abnormal state is the visual field impairment, that the driver is in a state where the driver has acquired compensatory action for the visual field impairment.

5. The driver state determination apparatus according to claim 3, wherein the controller is configured to:

detect a frequency of the driver's saccade based on of movement of the driver's sightline; and determine that the driver is in the abnormal state in the case where the saccade frequency is equal to or lower than a second threshold.

6. The driver state determination apparatus according to claim 3, further comprising:

an information output device that outputs information to the driver, wherein the controller is configured to cause the information output device to output information indicating that the driver suffers from the visual field impairment in the case where the controller determines that the driver is in the state of being unaware of the visual field impairment.

7. The driver state determination apparatus according to claim 2, further comprising an information output device that outputs information to the driver, wherein the controller is configured to cause the information output device to output information indicating that the driver suffers from the visual field impairment in the case where the controller determines that the driver is in the state of being unaware of the visual field impairment or indicating that the driver suffers from the attention dysfunction in the case where the controller determines that the abnormal state is the attention dysfunction.

8. The driver state determination apparatus according to claim 1, wherein the controller is configured to determine, in the case where the controller determines that the driver is not in the abnormal state and where the controller has determined in the past that the driver's abnormal state is the visual field impairment, that the driver is in a state where the driver has acquired compensatory action for the visual field impairment.

9. The driver state determination apparatus according to claim 1, wherein the controller is configured to:

detect a frequency of the driver's saccade based on of movement of the driver's sightline; and determine that the driver is in the abnormal state in the case where the saccade frequency is equal to or lower than a threshold.

10. The driver state determination apparatus according to claim 1, further comprising:

an information output device that outputs information to the driver, wherein the controller is configured to cause the information output device to output information indicating that the driver suffers from the visual field impairment in the case where the controller determines that the driver is in the state of being unaware of the visual field impairment.

11. A driver state determination circuit for determining a state of a driver who drives a vehicle, the driver state determination circuit being configured to:

receive the driver's sightline detected by a sightline detector;

receive the driver's head behavior detected by a head behavior detector; and determine the driver's state based on the driver's sightline and head behavior, including determine whether the driver is in an abnormal state based on movement of the driver's sightline;

on condition that the driver is in the abnormal state, determine whether the driver's abnormal state is a visual field impairment or not based on a change in each of a yaw angle and a pitch angle of the driver's head; and on condition that the driver's abnormal state is the visual field impairment, determine that the driver is aware of the visual field impairment when there is a direction in which the driver's sightline is not directed within a visual field of the driver, and determine that the driver is unaware of the visual field impairment when there is no direction in which the driver's sightline is not directed within a visual field of the driver.

12. The driver state determination circuit according to claim 11, wherein, on condition that the driver's abnormal state is not the visual field impairment, the driver state determination circuit is configured to determine that the driver's abnormal state is an attention dysfunction.

13. The driver state determination circuit according to claim 12, wherein, on condition that the driver's abnormal state is in the abnormal state, the driver state determination circuit is configured to determine that the driver's abnormal state is the visual field impairment when an amplitude of each of the yaw angle and the pitch angle of the driver's head is equal to or higher than a first threshold, and determine that the driver's abnormal state is the attention dysfunction when the amplitude of each of the yaw angle and the pitch angle of the driver's head is lower than the first threshold.

14. The driver state determination circuit according to claim 13, wherein, on condition that the driver is not in the abnormal state and the driver state determination circuit has determined in the past that the driver's abnormal state is the visual field impairment, the driver state determination circuit is configured to determine that the driver is in a state where the driver has acquired compensatory action for the visual field impairment.

15. The driver state determination circuit according to claim 13, wherein the driver state determination circuit is configured to:

detect a frequency of the driver's saccade based on of movement of the driver's sightline; and determine that the driver is in the abnormal state in the case where the saccade frequency is equal to or lower than a second threshold.

16. The driver state determination circuit according to claim 11, wherein, on condition that the driver is not in the abnormal state and the driver state determination circuit has determined in the past that the driver's abnormal state is the visual field impairment, the driver state determination circuit is configured to determine that the driver is in a state where the driver has acquired compensatory action for the visual field impairment.

17. The driver state determination circuit according to claim 11, wherein the driver state determination circuit is configured to:

detect a frequency of the driver's saccade based on of movement of the driver's sightline; and determine that the driver is in the abnormal state in the case where the saccade frequency is equal to or lower than a threshold.

18. A non-transitory computer readable storage device having computer readable instructions that when executed by circuitry cause the circuitry to:

receive the driver's sightline detected by a sightline detector;

receive the driver's head behavior detected by a head behavior detector; and determine the driver's state based on the driver's sightline and head behavior, including determine whether the driver is in an abnormal state based on movement of the driver's sightline;

on condition that the driver is in the abnormal state, determine whether the driver's abnormal state is a visual field impairment or not based on a change in each of a yaw angle and a pitch angle of the driver's head; and on condition that the driver's abnormal state is the visual field impairment, determine that the driver is aware of the visual field impairment when there is a direction in which the driver's sightline is not directed within a visual field of the driver, and determine that the driver is unaware of the visual field impairment when there is no direction in which the driver's sightline is not directed within a visual field of the driver.

* * * * *